United States Patent
Kunhiraman et al.

(10) Patent No.: US 12,148,230 B2
(45) Date of Patent: Nov. 19, 2024

(54) SYSTEM AND METHOD FOR NON-INVASIVE OPERATOR HEALTH MONITORING

(71) Applicant: Rockwell Collins, Inc., Cedar Rapids, IA (US)

(72) Inventors: Prajitha Kunhiraman, Bengaluru (IN); Carlo L. Tiana, Goldendale, WA (US); Amrit Chatterjee, Hyderabad (IN)

(73) Assignee: Rockwell Collins, Inc., Cedar Rapids, IA (US)

( * ) Notice: Subject to any disclaimer, the term of this patent is extended or adjusted under 35 U.S.C. 154(b) by 220 days.

(21) Appl. No.: 18/070,910

(22) Filed: Nov. 29, 2022

(65) Prior Publication Data

US 2024/0071107 A1    Feb. 29, 2024

(30) Foreign Application Priority Data

Aug. 24, 2022   (IN) .............................. 202211048227

(51) Int. Cl.
| | |
|---|---|
| *G06V 40/16* | (2022.01) |
| *A61B 5/0205* | (2006.01) |
| *G06F 3/01* | (2006.01) |
| *G06V 20/59* | (2022.01) |

(52) U.S. Cl.
CPC .......... *G06V 20/597* (2022.01); *A61B 5/0205* (2013.01); *G06F 3/013* (2013.01); *G06V 40/171* (2022.01); *G06V 40/176* (2022.01)

(58) Field of Classification Search
CPC .................................................. G06V 40/176
See application file for complete search history.

(56) References Cited

U.S. PATENT DOCUMENTS

| | | |
|---|---|---|
| 9,102,417 B1 | 8/2015 | Young |
| 9,826,941 B1 | 11/2017 | Serovy et al. |
| 10,058,277 B2 | 8/2018 | Kranz et al. |

(Continued)

FOREIGN PATENT DOCUMENTS

| | | |
|---|---|---|
| CN | 204839480 U | 12/2015 |
| CN | 111493897 A | 8/2020 |

(Continued)

OTHER PUBLICATIONS

Extended European Search Report dated Jan. 22, 2024; European Application No. 23193178.3.

(Continued)

*Primary Examiner* — Y Lee
(74) *Attorney, Agent, or Firm* — Suiter Swantz IP

(57) ABSTRACT

A method for non-invasive operator health monitoring is disclosed. The method may include receiving at least one of one or more images or one or more videos of tracked one or more facial features of a pilot from one or more pilot monitoring devices. The one or more tracked facial features may include at least one of a pilot's eyes, mouth, head posture, forehead, or cheek. The method may include determining at least one of one or more eye tracking parameters, one or more mouth tracking parameters, one or more head tracking parameters, or an emotion of the pilot. The method may include determining a pilot health monitoring value based on at least one of the determined one or more eye tracking parameters, the determined one or more mouth tracking parameters, the one or more head tracking parameters, or the determined emotion of the pilot.

12 Claims, 14 Drawing Sheets

(56) References Cited

U.S. PATENT DOCUMENTS

| | | |
|---|---|---|
| 10,357,195 B2 | 7/2019 | Beck et al. |
| 10,405,807 B2 | 9/2019 | Draeger et al. |
| 10,419,053 B2 | 9/2019 | Ruttler et al. |
| 10,426,393 B2 | 10/2019 | Bosworth et al. |
| 2016/0027336 A1 | 1/2016 | Towers et al. |
| 2018/0186234 A1 | 7/2018 | Mestha et al. |
| 2021/0034053 A1 | 2/2021 | Nikolic et al. |
| 2021/0188291 A1 | 6/2021 | el Kaliouby et al. |
| 2022/0070644 A1 | 3/2022 | Möhlmann et al. |
| 2022/0230522 A1 | 7/2022 | Myers |

FOREIGN PATENT DOCUMENTS

| | | |
|---|---|---|
| CN | 111613329 A | 9/2020 |
| CN | 114742090 A | 7/2022 |
| IN | 201921042164 A | 11/2019 |
| IN | 202114052628 A | 2/2022 |
| KR | 102270529 B1 | 6/2021 |

OTHER PUBLICATIONS

Hu Xinyun et al. "Detecting fatigue in car drivers and aircraft pilots by using non-invasive measures: The value of differentiation of sleepiness and mental fatigue", Journal of Safety Research, Pergamon, Amsterdam, NL, vol. 72, Jan. 14, 2020, pp. 713-187.

B. Mandal, et al., "Towards Detection of Bus Driver Fatigue Based on Robust Visual Analysis of Eye State," in IEEE Transactions on Intelligent Transportation Systems, vol. 18, No. 3, pp. 545-557, Mar. 2017, doi: 10.1109/TITS.2016.2582900.

SYSTEM AND METHOD FOR NON-INVASIVE OPERATOR HEALTH MONITORING

CROSS-REFERENCE TO RELATED APPLICATIONS

The present application claims the benefit of India Provisional Application No. 202211048227, entitled SYSTEM AND METHOD FOR NON-INVASIVE OPERATOR HEALTH MONITORING, filed Aug. 24, 2022, which is incorporated by reference in the entirety.

BACKGROUND

Human error is one of the direct factors that impacts aviation safety. The operator's health is one factor that contributes to human error. There is a need to find ways to minimize these humans error.
Additionally, as some operators shift to a single pilot system, there is a need to find ways to monitor the single pilot's health via non-human or substantially automated systems.

SUMMARY

A system is disclosed, in accordance with one or more embodiments of the present disclosure. The system includes one or more pilot monitoring devices configured to track one or more facial features of a pilot, the one or more tracked facial features including at least one of a pilot's eyes, a pilot's mouth, a pilot's head posture, a pilot's forehead, or a pilot's cheek, the one or more pilot monitoring devices configured to generate at least one of one or more images or one or videos of the tracked one or more facial features of the pilot. The system further includes one or more controllers communicatively coupled to the one or more imaging devices, the one or more controllers including one or more processors configured to execute a set of program instructions stored in memory, the set of program instructions configured to cause the one or more processors to: receive the at least one of the one or more images or the one or more videos from the one or more pilot monitoring devices; determine at least one of one or more eye tracking parameters, one or more mouth tracking parameters, one or more head tracking parameters, or an emotion of the pilot based on the received one or more mages or one or more videos; determine a pilot health monitoring value based on at least one of the determined one or more eye tracking parameters, the determined one or more mouth tracking parameters, the one or more head tracking parameters, or the determined emotion of the pilot.

In some embodiments, the one or more pilot monitoring devices may include one or more cameras.

In some embodiments, the one or more cameras may include one or more cockpit cameras.

In some embodiments, the one or more cameras may include one or more head worn device cameras.

In some embodiments, the one or more processors may be configured to determine the pilot health monitoring value based on at least one of the determined one or more eye tracking parameters, the determined one or more mouth tracking parameters, the one or more head tracking parameters, or the determined emotion of the pilot using one of a rule-based algorithm or a machine learning model stored in the memory of the one or more controllers.

In some embodiments the one or more processors may be configured to determine the pilot health monitoring value based on at least one of the determined one or more eye tracking parameters, the determined one or more mouth tracking parameters, or the one or more head tracking parameters using one or more predetermined thresholds stored in the memory of the one or more controllers.

In some embodiments, the one or more eye tracking parameters may include at least one of a blink frequency, a percentage of eye lid closure, an average eye closure, a blink type, an average eye closure speed, an interblink duration, an eye gaze state, or an eye gaze frequency.

In some embodiments, the one or more mouth tracking parameters may include a yawn frequency.

In some embodiments, the one or more head tracking parameters may include a head tilt angle.

In some embodiments, the pilot health monitoring value may include a sleep scale score.

In some embodiments, the pilot health monitoring value may include a fatigue scale score.

In some embodiments, the pilot health monitoring value may include a stress score.

In some embodiments, the set of program instructions may be configured to cause the one or more processors to determine a color skin intensity value of at least one of the pilot's forehead or the pilot's cheeks and determine at least one a pulse rate, a blood pressure, or a respiration rate based on the determined skin intensity value In some embodiments, the determine at least one a pulse rate, a blood pressure, a respiration rate based on the determined skin color intensity value may further comprises deriving a power spectrum of one or more pixel values computed from at least one of the pilot's forehead or the pilot's cheeks.

A method is disclosed, in accordance with one or more embodiments of the present disclosure. The method includes receiving at least one of one or more images or one or more videos of one or more tracked facial features of a pilot from one or more pilot monitoring devices, the one or more tracked facial features including at least one of a pilot's eyes, a pilot's mouth, a pilot's head posture, a pilot's forehead, or a pilot's cheek. The method includes determining at least one of one or more eye tracking parameters, one or more mouth tracking parameters, one or more head tracking parameters, or an emotion of the pilot based on the received one or more mages or one or more videos. The method includes determining a pilot health monitoring value based on at least one of the determined one or more eye tracking parameters, the determined one or more mouth tracking parameters, the one or more head tracking parameters, or the determined emotion of the pilot.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are examples and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the disclosure are disclosed in the following detailed description and the accompanying drawings. The drawings are not necessarily to scale.

In general, operations of disclosed processes may be performed in an arbitrary order, unless otherwise provided in the claims. In the drawings:

DETAILED DESCRIPTION OF THE INVENTION

Figure 1A:
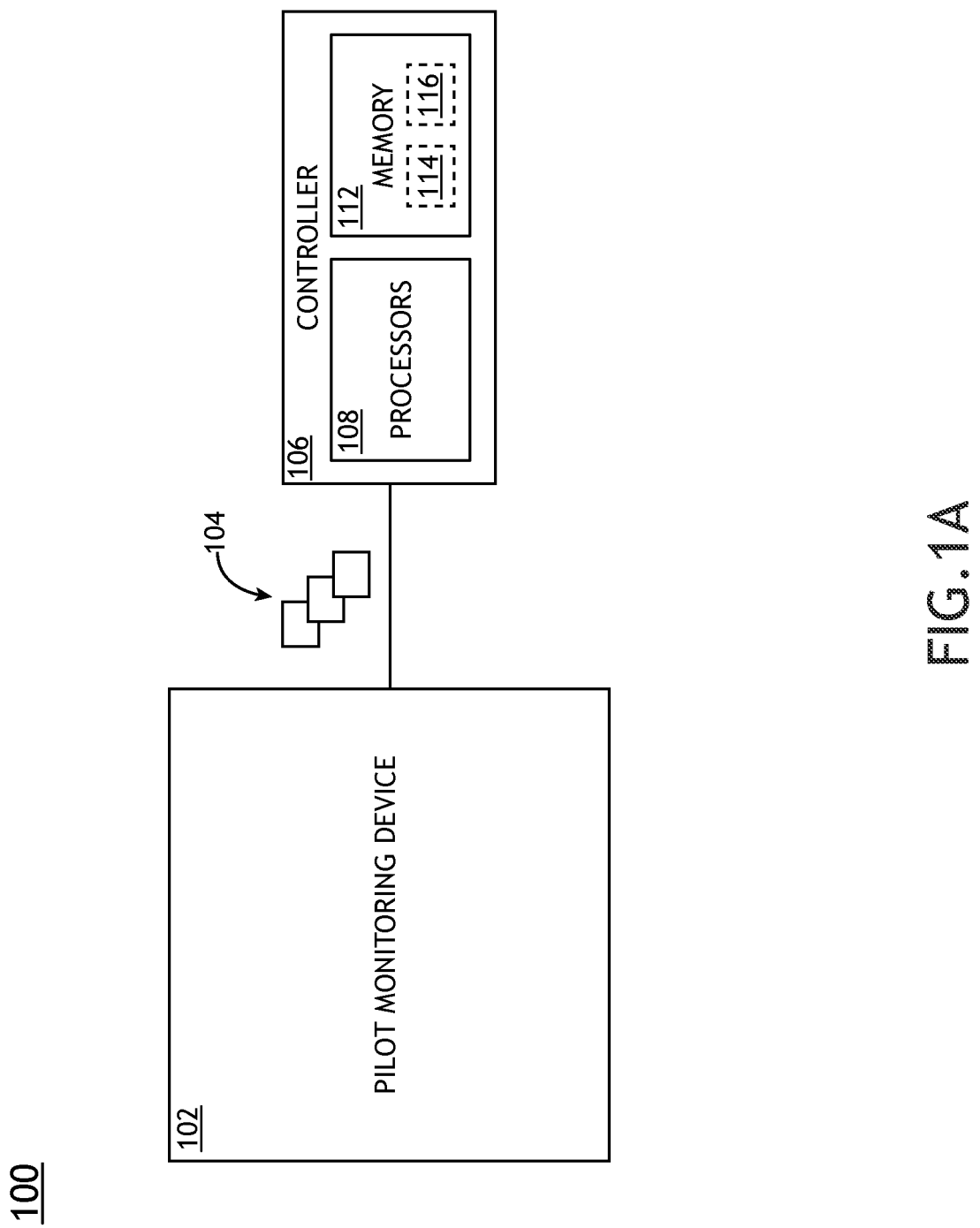
FIG. 1A illustrates a simplified block diagram of a system for non-invasive operator health monitoring, in accordance with one or more embodiments of the disclosure.

Reference will now be made in detail to the subject matter disclosed, which is illustrated in the accompanying drawings.

Before explaining one or more embodiments of the disclosure in detail, it is to be understood the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure the embodiments disclosed herein may be practiced without some of these specific details. In other instances, well-known features may not be described in detail to avoid unnecessarily complicating the instant disclosure.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination of or sub-combination of two or more such features, along with any other features which may not necessarily be expressly described or inherently present in the instant disclosure.

Human error is one of the direct factors that impacts aviation safety. The operator's health is one factor that contributes to human error. There is a need to find ways to minimize these humans errors. Additionally, current cockpit operations today involve crew resource management procedures where various crewmembers (or other personnel) cross check each other for critical. As some operators shift to a single pilot system, there is a need to find ways to monitor the single pilot's health via non-human or substantially automated systems.

Existing systems are invasive and require a pilot to wear an additional wearable device (or other sensors) to monitor the physiological signals of the pilot (e.g., blood pressure, heart rate, etc.). The invasive nature of the existing systems may cause discomfort for the pilot. Further, the use of multiple sensors to calculate various parameters is costly.

As such, it would be desirable to provide a system and method for non-invasive pilot health monitoring that cures one or more of the shortfalls of the previous approaches discussed above. The system should be non-invasive (e.g., not require the pilot to wear additional devices/sensors). The system should rely on vision-based techniques to calculate a sleep value, fatigue value, and/or a stress value. The system should provide an accurate assessment of a pilot's health status pre-flight, post-flight, and/or during flight.

Figure 1B:
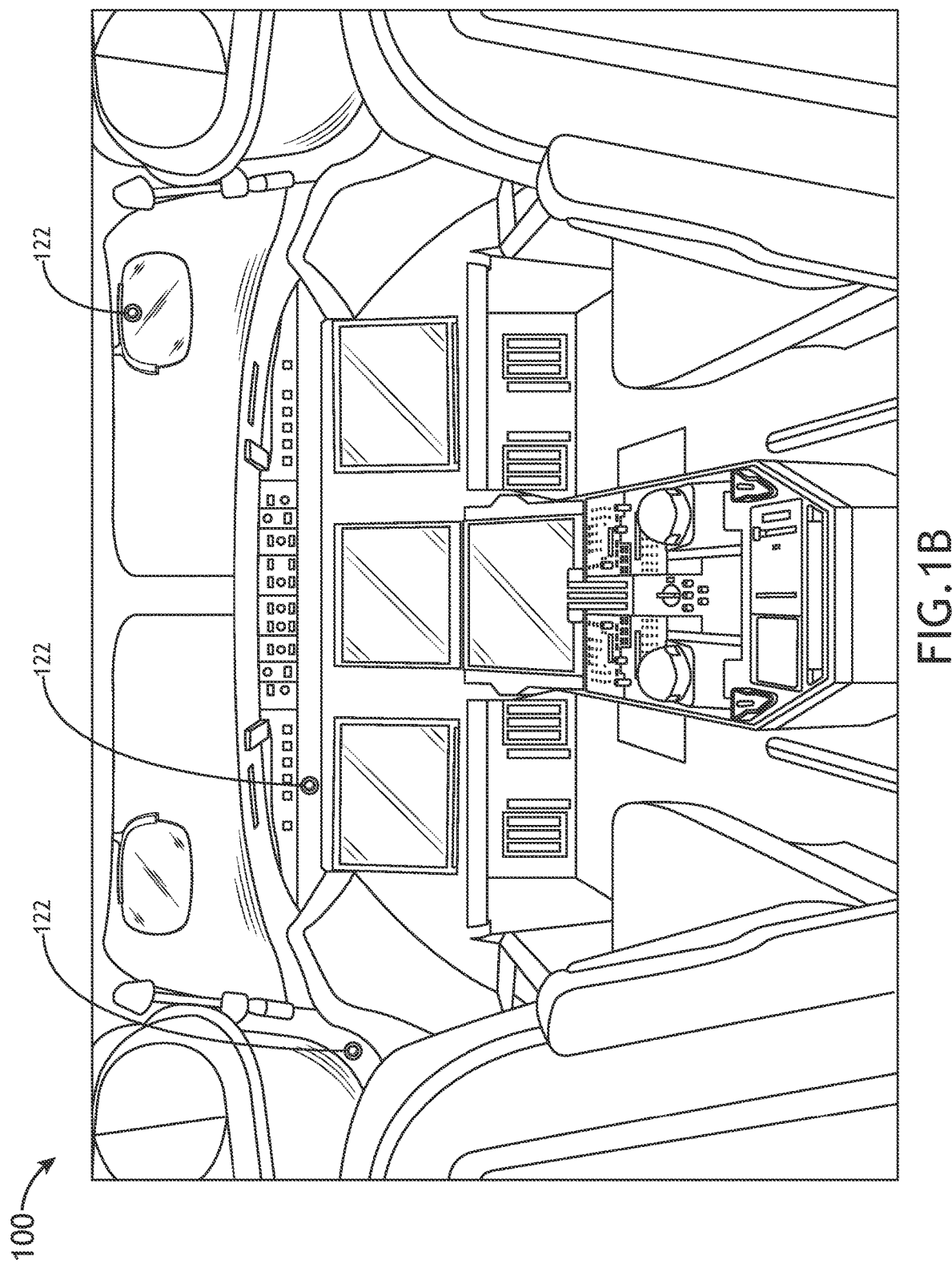
FIG. 1B illustrates a simplified schematic of an aircraft cockpit including a system for non-invasive operator health monitoring, in accordance with one or more embodiments of the disclosure.
Figure 1C:
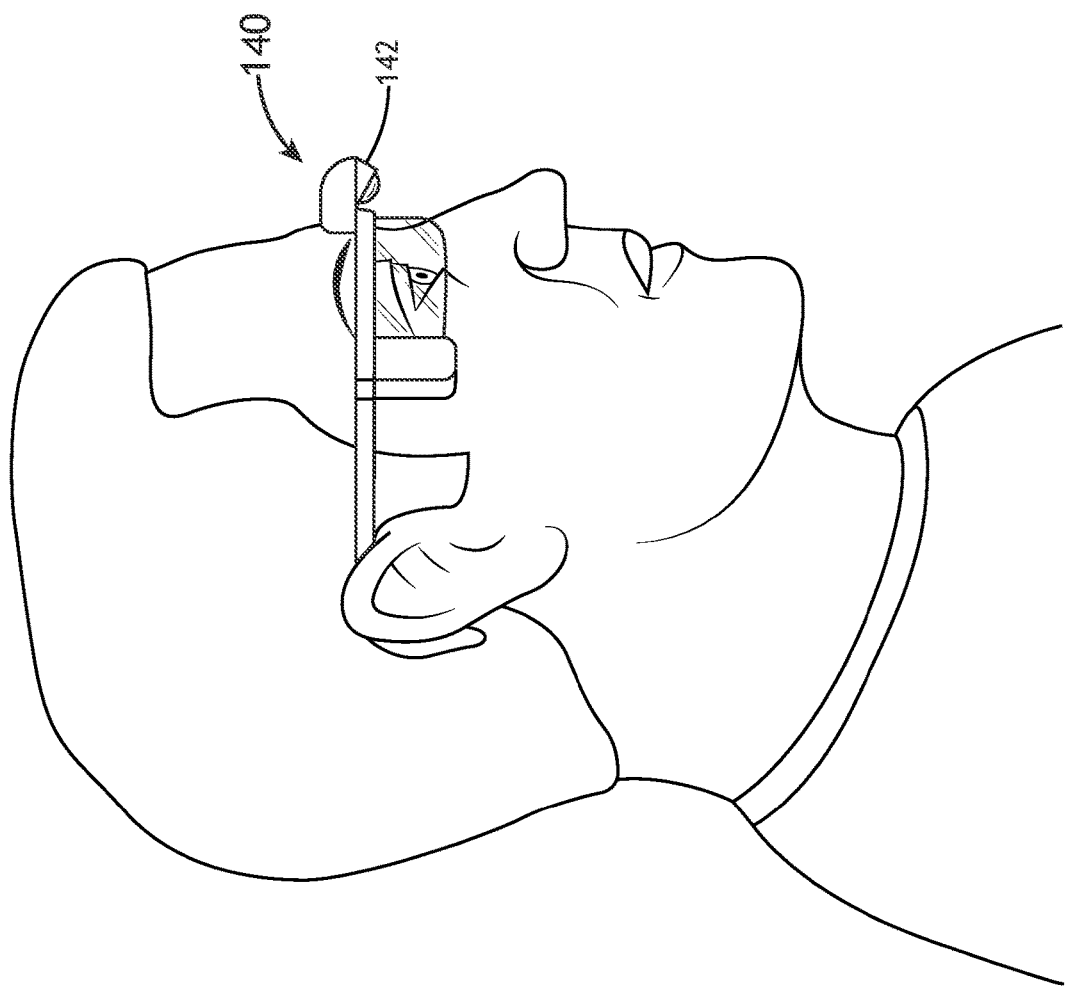
FIG. 1C illustrates a simplified schematic of a head worn device including a system for non-invasive operator health monitoring, in accordance with one or more embodiments of the disclosure.

FIG. 1A illustrates a simplified block diagram of the system 100 for non-invasive operator health monitoring, in accordance with one or more embodiments of the present disclosure. FIG. 1B illustrates a simplified schematic of an aircraft cockpit including a system for non-invasive operator health monitoring, in accordance with one or more embodiments of the disclosure. FIG. 1C illustrates a simplified schematic of a head worn device including a system for non-invasive operator health monitoring, in accordance with one or more embodiments of the disclosure.

The system 100 may include one or more pilot monitoring devices 102 configured to track one or more facial features of a vehicle operator (e.g., pilot). For example, the one or more pilot monitoring devices 102 may be configured to track one or more facial features including, but not limited to, at least one of a pilot's eyes, a pilot's mouth, a pilot's head posture, a pilot's forehead, a pilot's cheek, or the like.

The one or more pilot monitoring devices 102 may configured to generate at least one of one or more images 104 or one or more videos 104 including the tracked one or more facial features of the pilot. For example, as shown in FIG. 1B, the one or more pilot monitoring devices 102 may include one or more cameras 122 coupled to one or more portions of a cockpit (such as the cockpit 120 shown in FIG. 1B). In one instance, the one or more cameras 122 may include at least one camera 122 mounted straight facing (e.g., in front of) the pilot. In another instance, the one or more cameras 122 may include at least one camera 122 mounted to the left and/or right of the pilot. In another instance, the one or more cameras 122 may include at least one camera 122 mounted above the pilot (e.g., facing downward). It is noted that the camera 122 may be mounted in any suitable location within the cockpit to accurately capture one or more images and/or videos 104 of the tracked facial features of the pilot.

By way of another example, as shown in FIG. 1C, the one or more pilot monitoring devices 102 may include one or more cameras 142 coupled to one or more portions of a head worn device (HWD) (such as the HWD 140 shown in FIG. 1C). For instance, as shown in FIG. 1C, the one or more cameras 142 may be positioned in the middle of the HWD 140 at a flexible angle and position inside the HWD such that the one or more cameras 142 may capture one or more images or videos of the pilot's face (e.g., from a top angle). It is noted that the cockpit and HWD shown in FIGS. 1B-1C are provided merely for illustrative purposes and shall not be construed as limiting the scope of the present disclosure.

The system may include one or more controllers 106 may be communicatively coupled to the one or more pilot monitoring devices 102. In this regard, the one or more processors 108 of the one or more controllers 106 may be configured to generate one or more control signals to cause the one or more processors 108 to carry out various steps of the present disclosure.

It is noted that the one or more controllers 106 may be housed in a common housing of the pilot monitoring device 102 or housed external to the pilot monitoring device 102. As such, FIGS. 1A-1C are provided merely for illustrative purposes and shall not be construed as limiting the scope of the present disclosure.

In some embodiments, the system 100 may include a rule based algorithm 114, such that the one or more processors are configured to determine a pilot health monitoring value using the rule based algorithm 114. For example, the one or more controllers 106 may include rule based algorithm 114 stored in memory 110.

In some embodiments, the system 100 may include a machine learning algorithm 114, such that the one or more processors are configured to determine a pilot health monitoring value using the machine learning algorithm 114. For example, the one or more controllers 106 may include a machine learning algorithm 114 stored in memory 110.

The rule based/machine learning algorithm 114 may be configured to determine a pilot monitoring value based on one or more biometric parameters derived from the received one or more images or one or more videos, as discussed further herein.

In some embodiments, the system 100 may include a database 116 including one or more predetermined thresholds, such that the one or more processors may be configured to determine a pilot health monitoring value based on the one or more predetermine thresholds. For example, the one or more controllers 106 may include a database 116 stored in memory 110. The one or more predetermined thresholds may be compared to one or more biometric parameters derived from the received one or more images or one or more videos to determine a pilot monitoring value, as discussed further herein. For example, the one or more predetermined thresholds may include one or more predetermined thresholds specific to an individual pilot. By way of another example, the one or more predetermined thresholds may include one or more predetermined thresholds specific a pilot class (e.g., aging pilots, different pilot genders, different pilot physical characteristics). By way of another example, the one or more predetermined thresholds may include one or more predetermined thresholds optimized or calibrated for a plurality of flight phases.

The system 100 may further include a user interface communicatively coupled to the one or more controllers 106. The user interface may include a user input device and a display. The user input device may be configured to receive one or more input commands from a user, the one or more input commands may be configured to input data into the system.

It is noted herein that the one or more components of system 100 may be communicatively coupled to the various other components of system 100 in any manner known in the art. For example, the one or more processors 108 may be communicatively coupled to each other and other components via a wireline (e.g., copper wire, fiber optic cable, and the like) or wireless connection (e.g., RF coupling, IR coupling, WiMax, Bluetooth, 3G, 4G, 4G LTE, 5G, and the like). By way of another example, the controller 106 may be communicatively coupled to one or more components of detection sub-system 102 via any wireline or wireless connection known in the art.

The one or more processors 108 may include any one or more processing elements known in the art. In this sense, the one or more processors 108 may include any microprocessor device configured to execute algorithms and/or program instructions. In general, the term "processor" may be broadly defined to encompass any device having one or more processing elements, which execute a set of program instructions from a non-transitory memory medium (e.g., the memory 110), where the one or more sets of program instructions are configured to cause the one or more processors 108 to carry out any of one or more process steps.

The memory 110 may include any storage medium known in the art suitable for storing the one or more sets of program instructions executable by the associated one or more processors 108. For example, the memory 110 may include a non-transitory memory medium. For instance, the memory 110 may include, but is not limited to, a read-only memory (ROM), a random access memory (RAM), a magnetic or optical memory device (e.g., disk), a magnetic tape, a solid state drive, and the like. The memory 110 may be configured to provide display information to the user device 102. In addition, the memory 110 may be configured to store user input information from one or more user input devices. The memory 110 may be housed in a common controller housing with the one or more processors 108. The memory 110 may, alternatively or in addition, be located remotely with respect to the spatial location of the processors 108 and/or the one or more controllers 106. For instance, the one or more processors 108, the one or more controllers 106 may access a remote database, accessible through a network (e.g., internet, intranet, and the like) via one or more communication interfaces.

The one or more communication interfaces may be operatively configured to communicate with one or more components of the one or more controllers 106 and/or the one or more components of the system. For example, the one or more communication interfaces may also be coupled (e.g., physically, electrically, and/or communicatively) with the one or more processors 108 to facilitate data transfer between components of the one or more components of the one or more controllers 106 and/or the one or more components of the system 100 and the one or more processors 108. For instance, the one or more communication interfaces may be configured to retrieve data from the one or more processors 108, or other devices, transmit data for storage in the memory 110, retrieve data from storage in the memory 110, or the like.

In one embodiment, a user interface 110 is communicatively coupled to the controller 106. In one embodiment, the user interface 110 may include, but is not limited to, one or more desktops, tablets, smartphones, smart watches, or the like. In another embodiment, the user interface 110 includes a display 114 used to display data of the system 100 to a user. The display 114 of the user interface 110 may include any display known in the art. For example, the display 114 may include, but is not limited to, a liquid crystal display (LCD), an organic light-emitting diode (OLED) based display, or a CRT display. Those skilled in the art should recognize that any display device capable of integration with a user interface 110 is suitable for implementation in the present disclosure. In another embodiment, a user may input selections and/or instructions responsive to data displayed to the user via a user input device of the user interface 110.

Figure 2:
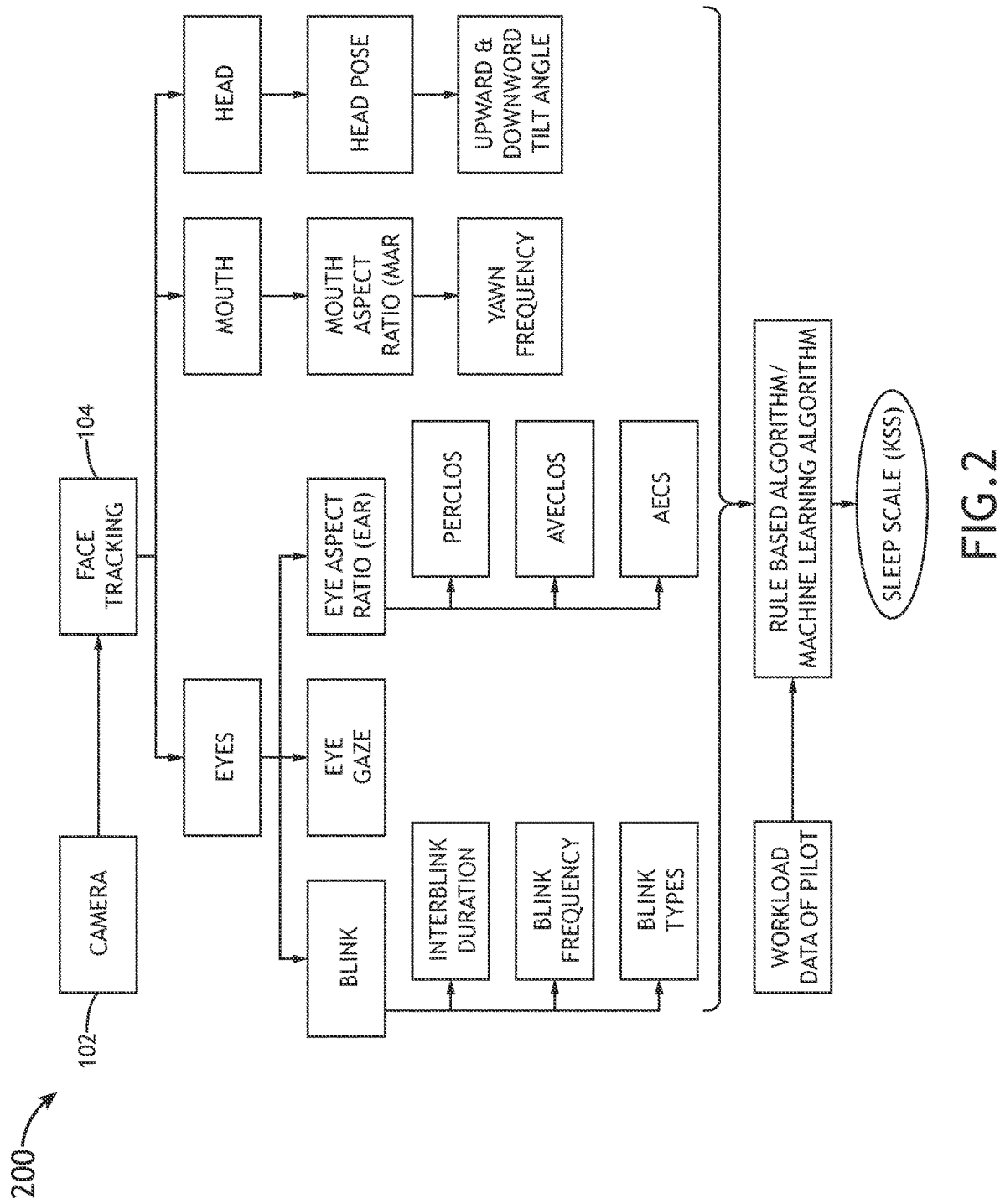
FIG. 2 illustrates a simplified block diagram of a method or processing for non-invasive operator health monitoring, in accordance with one or more embodiments of the disclosure.
Figure 3A:
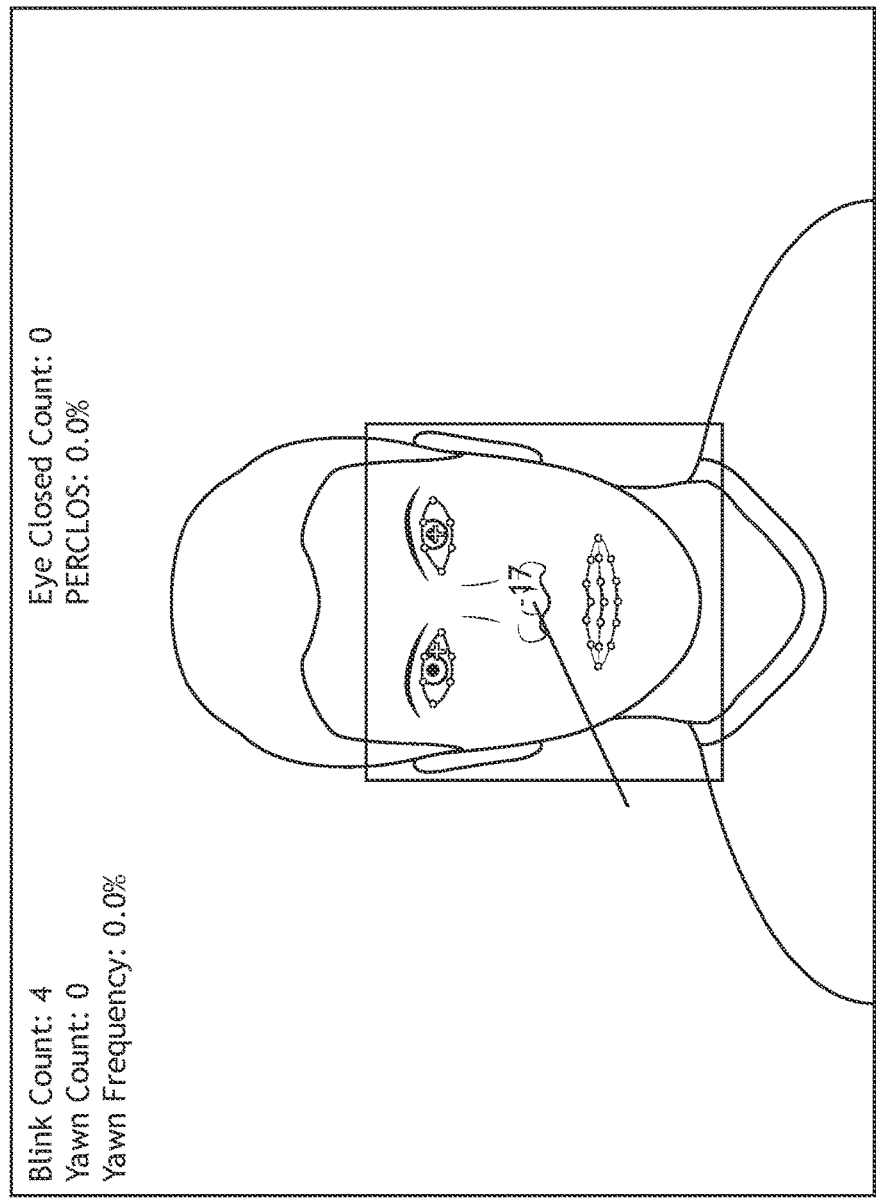
FIG. 3A illustrates a simplified schematic of face tracking images of the system for non-invasive operator health monitoring, in accordance with one or more embodiments of the disclosure.
Figure 3B:
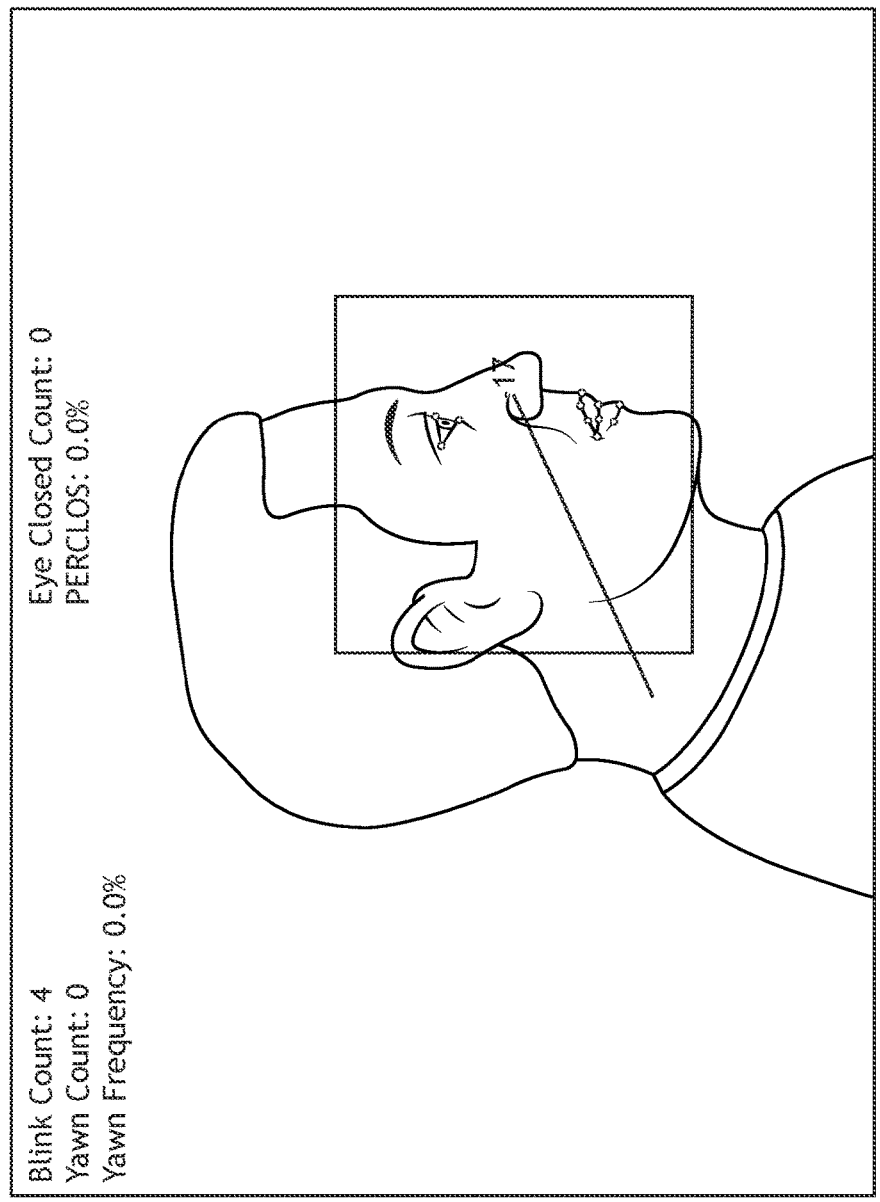
FIG. 3B illustrates a simplified schematic of face tracking images of the system for non-invasive operator health monitoring, in accordance with one or more embodiments of the disclosure.

FIG. 2 illustrates a simplified block diagram flow chart depicting a method or process 200 for determine a sleep scale value, in accordance with one or more embodiments of the present disclosure. FIGS. 3A-3B illustrate conceptual views of face tracking images, in accordance with one or more embodiments of the present disclosure.

The system 100 may be configured to determine one or more biometric parameters based on the received images/videos 104 including the tracked facial features.

For example, the one or more controllers 106 may be configured to determine one or more eye parameters. For instance, the one or more or eye parameters may include, but are not limited to, blink parameters (e.g., interblink duration, blink frequency, blink type, and the like), eye gaze parameters, eye aspect ratios (EAR) parameters (e.g., PERCLOS, AVECLOS, AECS, and the like), and the like.

Each of the eye parameters may be measured and averaged out for a given predetermined amount of time (e.g., a minute) and then used to determine the sleep scale value (e.g., using the rule based algorithm or the predetermined thresholds).

Each of the eye parameters may be determined by classifying the eye state as one of open or closed. For example, the one or more controllers 106 may be configured to measure the Eye Aspect Ratio (EAR). For purposes of the present disclosure, EAR may be the ratio of height to width of the eyes, where a value of 0 indicates closed state of eye and anything greater than 0 indicates the open state of eye. Based on this ratio's value and using a common threshold, the eye states are computed.

This EAR ratio's drop for one frame is computed as blink and longer than few frames is computed as eye closed state. With the blinks, their amplitude and time taken is used to differentiate them as short blink, long blink, very long blink, and Sleepy blink. Also, the time difference between blinks is computed as the interblink duration. The same EAR ratio is used to compute the PERCLOS, AVECLOS and AECS. The Eye gaze is computed by looking for the location of Iris center in the tracked frame. Iris tracking may be performed using one or more computer vision techniques. Further iris tracking may additionally and/or alternatively be performed using machine learning model tracking. From the Iris center detected, the eye gaze states are classified as Sleepy gaze, fixed gaze, and alert gaze.

By way of another example, the one or more controllers 106 may be configured to determine one or more mouth parameters. For instance, the one or more or mouth parameters 210 may include, but are not limited to, mouth aspect ratios (MAR) parameters, yawn frequency parameters, and the like.

It is noted that the mouth tracking helps in computing the yawns and their frequency. For example, the one or more controllers 106 may be configured to determine the MAR. For instance, the determined MAR and a predetermined threshold may be used to differentiate between yawn and the other state of mouth.

By way of another example, the one or more controllers 106 may be configured to determine one or more head tracking parameters. For instance, the one or more head tracking parameters may include, but are not limited to, head pose parameters, head tilt angle parameters, and the like.

The one or more controllers 106 may be configured to determine the head tilt angle parameters using the perspective-n-points method to project the points on to the 3D space using the 2D image points extracted using the computer vision techniques and the rotational and translational vectors are derived from it. These are then projected onto the 3D space from one point in the face, which is chosen here as the nose tip and the angle across the x and y axis is computed to determine the head tilting down or upright position is detected.

The system 100 may be configured to determine a sleep scale value based on the one or more determined biometric parameters. For example, the one or more controllers 106 may be configured to determine the sleep scale value based on the determined biometric parameters using a rule based/machine learning algorithm (such as the algorithm 114 stored in memory 110). By way of another example, the one or more controllers 106 may be configured to determine the sleep scale value based on the determined biometric parameters and one or more predetermined thresholds of a database (such as the database 116 stored in memory 110).

Each of these computed biometrics add on to the Sleep algorithm and then the maximum sleep scale is derived out of it. The sleep scale value may be determined according to the Karolinska Sleepiness Scale (KSS). For example, a percentage of eyelid closure (PERCLOS) may be determined. For instance, a percentage of time for which the eyes are closed for 80% or more may be determined. In this regard, a PERCLOS value greater than 30% (0.3) is considered as the sleepy stage and any value less than 15% (0.15) is considered as the alert stage. By way of another example, an average eye closure (AVECLOS) may be determined. For instance, the average time the eyes are fully closed over a predetermined amount of time (e.g., one minute) may be determined. By way of another example, average eye closure (AECS) may be determined. For instance, the speed of the eye closure may be determined for a predetermined amount of time. In this regard, a higher speed indicates alertness, while a lesser speed indicates signs of sleepiness. Based on the blink classification, the higher the sleep value, the longer the blinks are, and the slower the blinks are the lower the sleep value (e.g., classified as the alert stage). While based on the eye gaze state, a fixed gaze indicates that a person is entering the drowsy state, while a more the alert gaze indicates the Alert state and a more sleepy state indicates the Sleepy state. Interblink duration is related along with the blink count to the sleep scale, such that a higher blink count (with in the average range) and a lesser the blink duration indicates alertness. The head tilt angle computed also adds into the sleep scale, where a higher head tilt value directly corresponds to a high chance of sleepiness. Similarly, the yawn and blink frequency are also used for the Sleep scale, where a higher yawn frequency indicates a higher chance of sleepiness and a lower frequency indicates more alertness.

In some embodiments, the system 100 may be configured to received workload data of a pilot. For example, the one or more controllers 106 may be configured to receive the workload data of the pilot and use the data when computing the sleep scale value.

Figure 4:
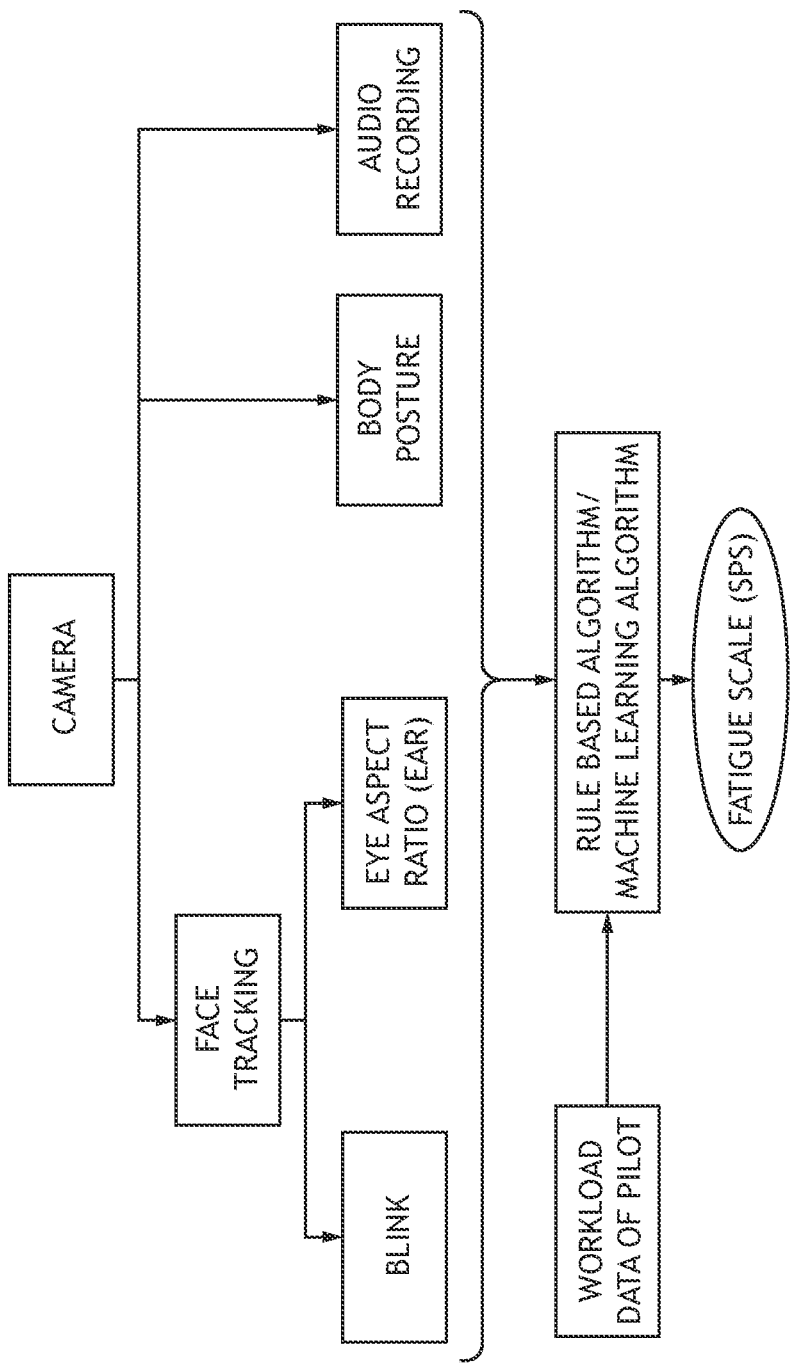
FIG. 4 illustrates a simplified block diagram of a method or processing for non-invasive operator health monitoring, in accordance with one or more embodiments of the disclosure.
Figure 5A:
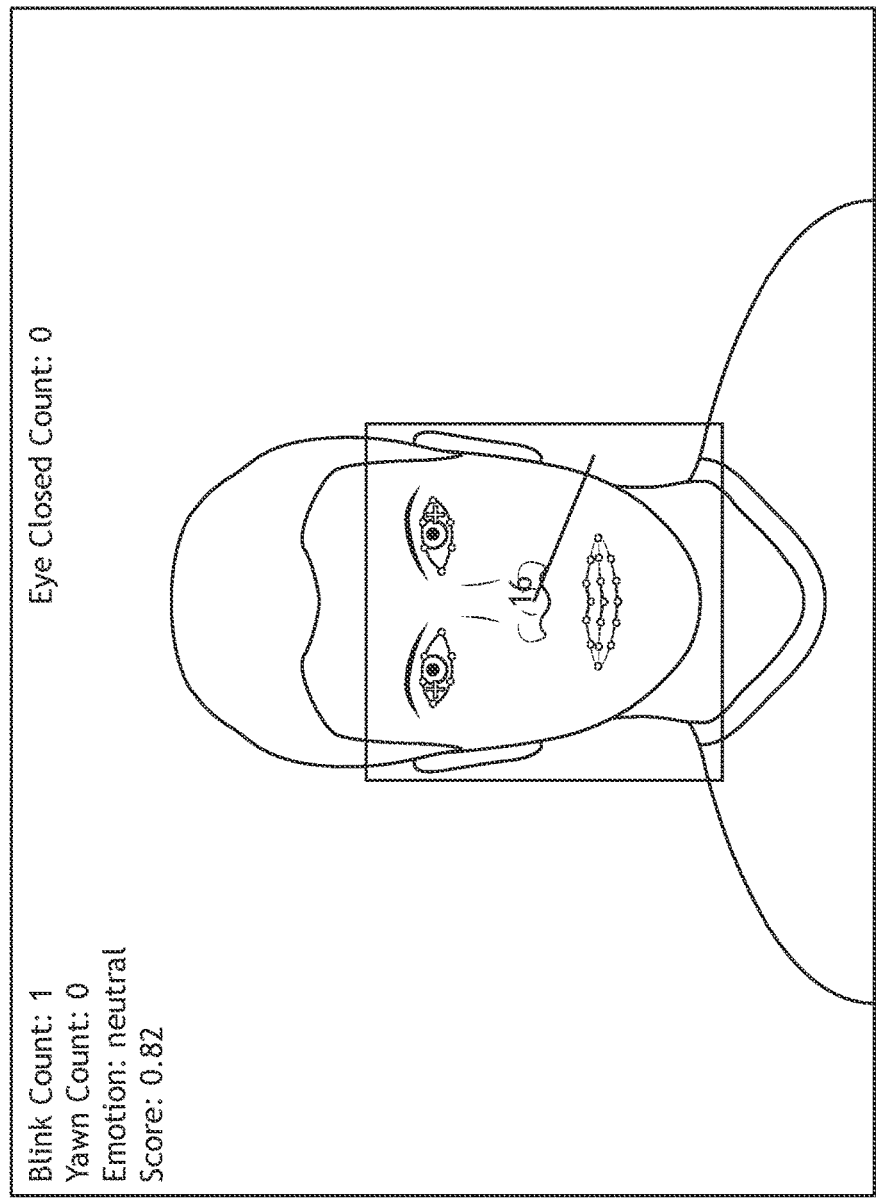
FIGS. 5A-5C illustrate simplified schematics of face tracking images of the system for non-invasive operator health monitoring, in accordance with one or more embodiments of the disclosure.
Figure 5B:
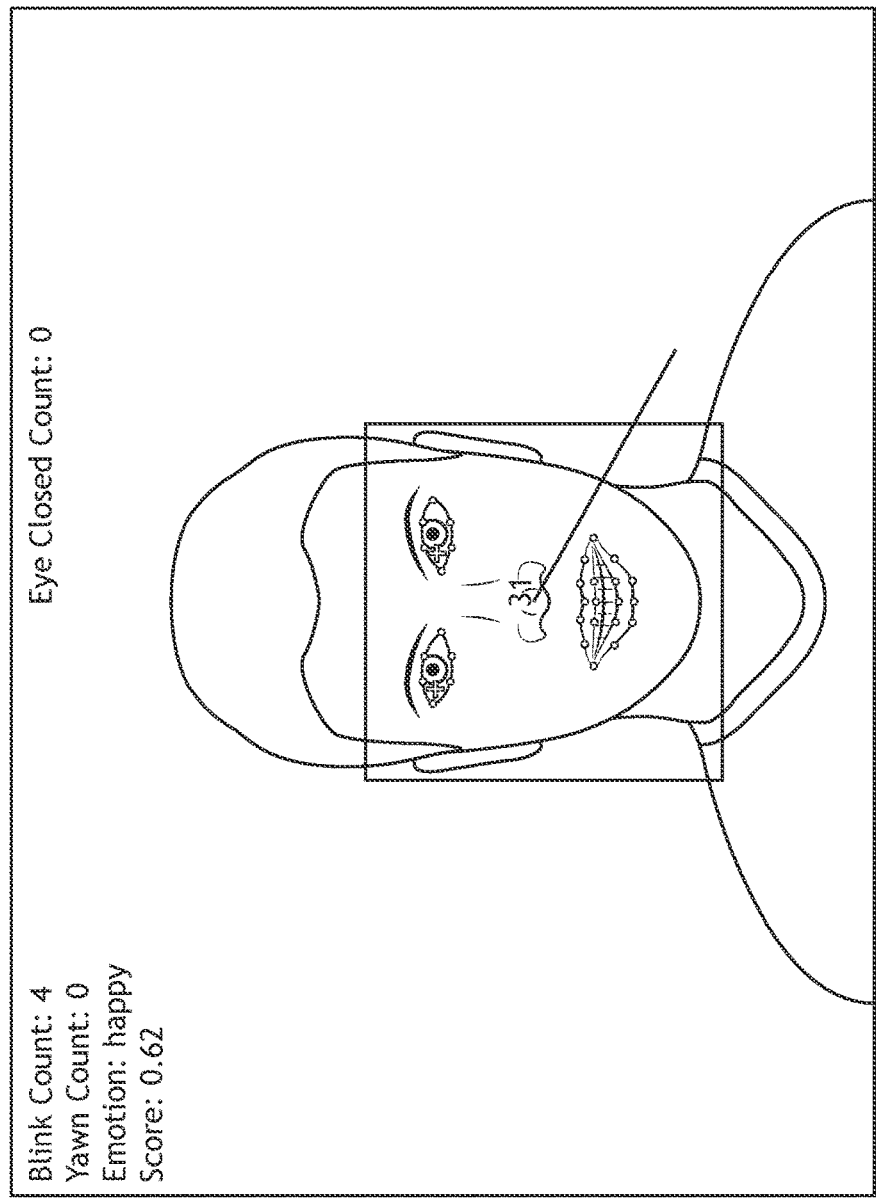
Figure 5C:
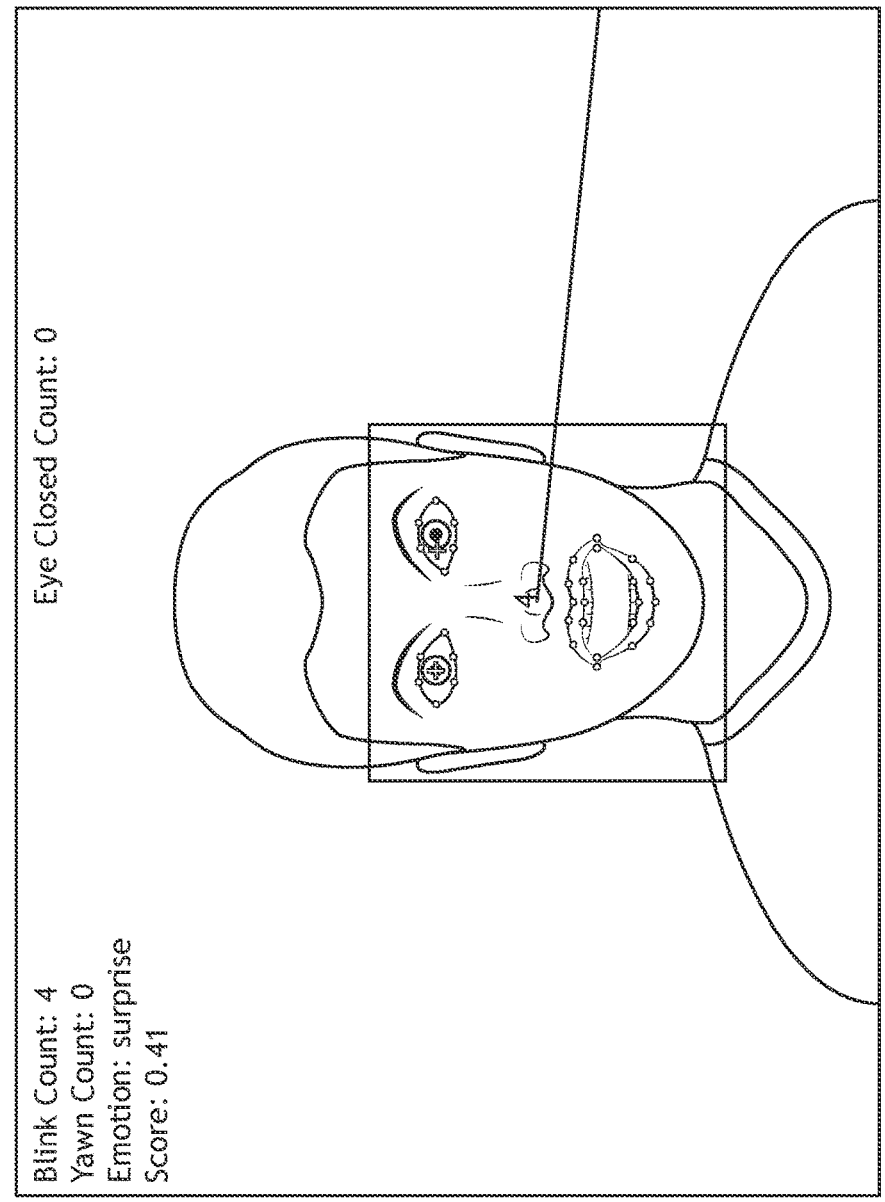

FIG. 4 illustrates a simplified block diagram flow chart depicting a method or process 400 for determine a fatigue scale value, in accordance with one or more embodiments of the present disclosure. FIGS. 5A-5C illustrate conceptual views of face tracking, in accordance with one or more embodiments of the present disclosure.

The system 100 may be further configured to detect one or more emotions of the pilot. For example, the one or more controllers 106 may be configured to detect at least one of anger, disgust, sadness, neutral, happy, surprise, or fear.

The system 100 may be configured to determine a fatigue scale value (based on Samn Prescili Fatigue Scale method) using the calculated sleep scale value (as previously discussed herein) and the detected emotions, where 1 indicates fully alert and 7 is fatigued (e.g., completely exhausted and tired). It is noted that the emotions that indicate high fatigue or entry into fatigue may include, but are not limited to, sad, anger, neutral, disgust, or the like. It is noted that the sleep scale may directly contribute to the fatigue computation. For example, the higher the sleep scale value the higher the chance of being fatigued. Further, the detection of negative emotions and low alert status may indicate/contribute to a higher fatigue scale value. In this regard, a lower fatigue scale value may be determined with a lower the sleep scale value, detection of positive emotions, and alert high gaze status.

In some embodiments, the system 100 may be configured to track a pilot's body posture. For example, the one or more pilot monitoring devices 102 may be configured to track the pilot's body posture during flight.

In some embodiments, the system 100 may be configured to capture audio from the cockpit. For example, the one or more pilot monitoring devices 102 may be configured to capture audio from the cockpit.

In some embodiments, the system 100 may be configured to receive flight status information from one or more on-board controllers of the aircraft. For example, the one or more controllers 106 may be configured to receive flight tracking and status information from one or more flight management systems on the aircraft.

Figure 6:
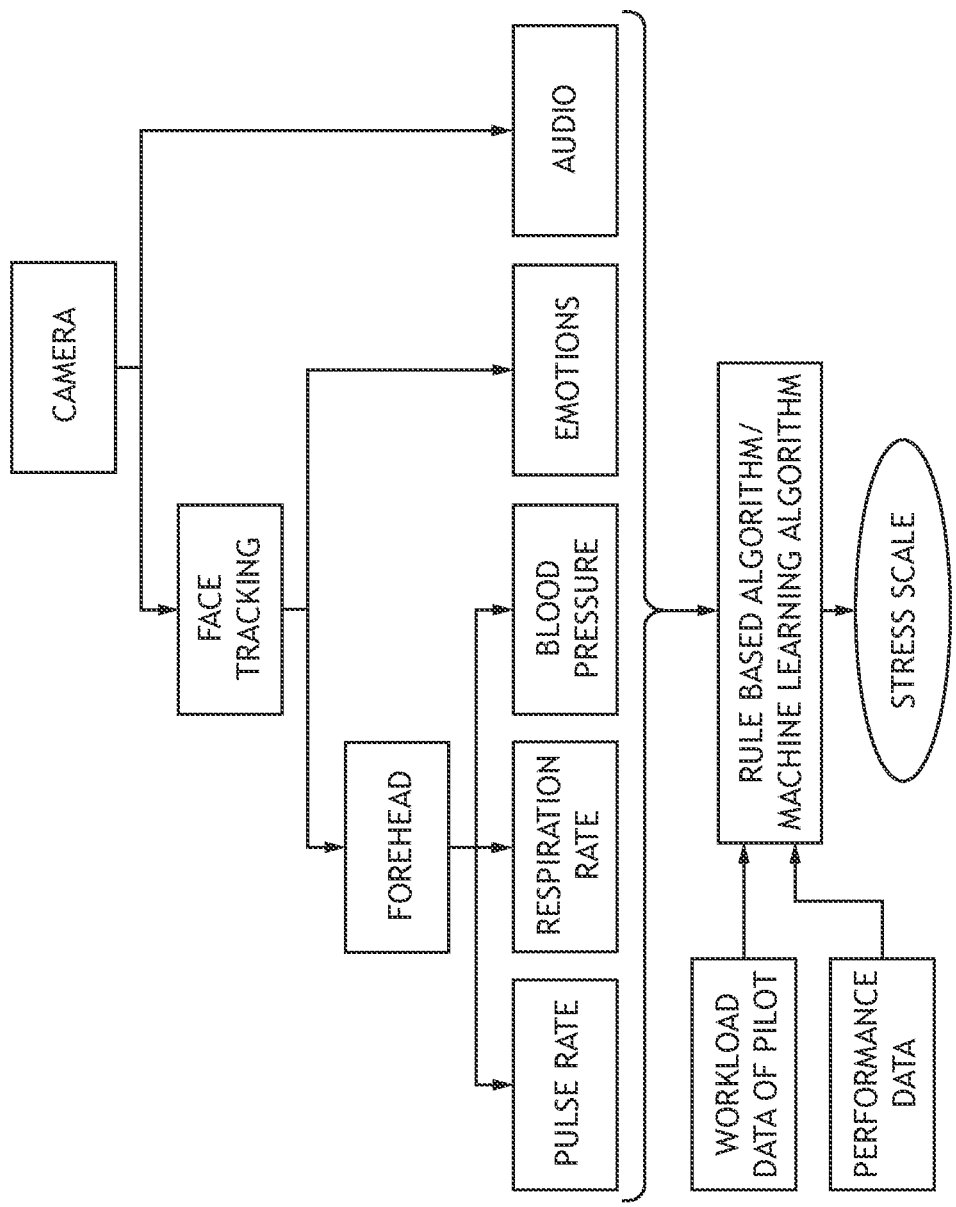
FIG. 6 illustrates a simplified block diagram of a method or processing for non-invasive operator health monitoring, in accordance with one or more embodiments of the disclosure.
Figure 7:
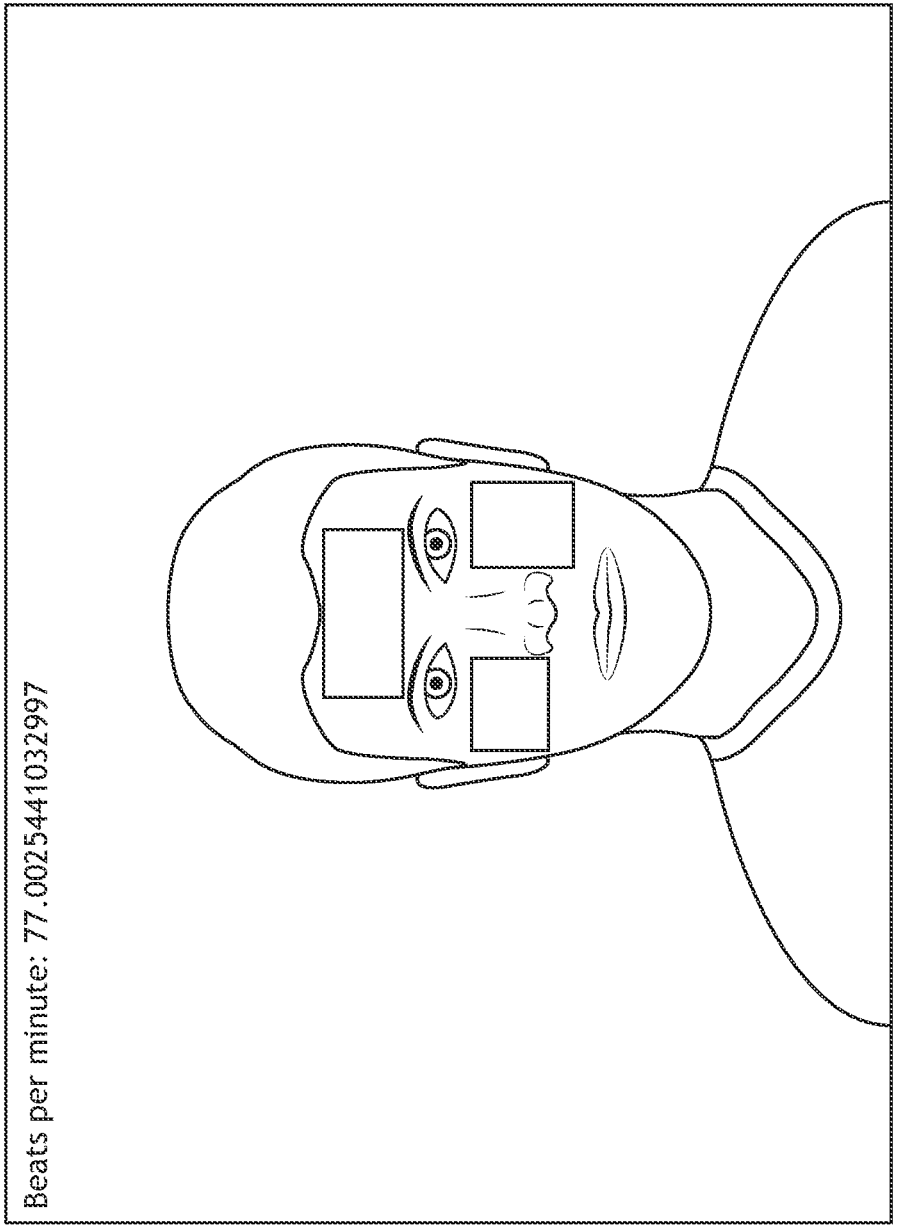
FIG. 7 illustrates a simplified schematic of face tracking images of the system for non-invasive operator health monitoring, in accordance with one or more embodiments of the disclosure.
Figure 8:
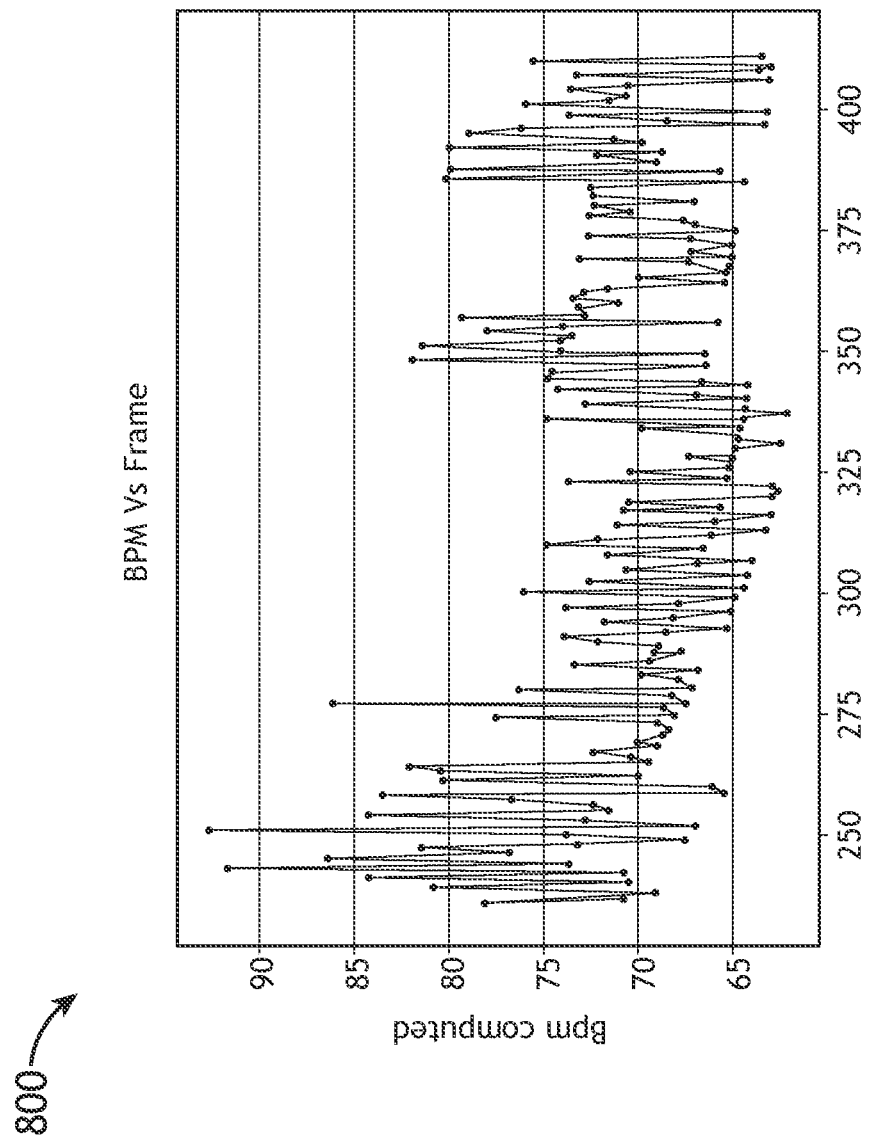
FIG. 8 illustrates a plot, in accordance with one or more embodiments of the disclosure.

FIG. 6 illustrates a simplified block diagram flow chart depicting a method or process 600 for determine a stress scale value, in accordance with one or more embodiments of the present disclosure. FIG. 7 illustrates a conceptual view of face tracking, in accordance with one or more embodiments of the present disclosure. FIG. 8 illustrates a plot 800, in accordance with one or more embodiments of the present disclosure.

The system 100 may be configured to determine a stress scale value based on a skin color intensity value. For example, the one or more controllers 106 may be configured to determine a skin intensity value of at least one of the pilot's forehead or the pilot's cheeks based on the received images/video 106. Further, the one or more controllers 106 may be configured to determine at least one a pulse rate, a blood pressure, or a respiration rate based on the determined skin intensity value and the detected emotion. For example, the one or more controllers 106 may be configured to determine at least one a pulse rate, a blood pressure, or a respiration rate based on the determined skin color intensity value by deriving a power spectrum of the pixel values computed from the region of interest (e.g., forehead, cheeks and the like). In this regard, the derived power spectrum may be used with a band pass filter to capture the desired output. This may be accomplished by monitoring and measuring the regular reddening of the skin on the pilot's face caused by the pilot's heartbeat, either directly or by means of frequency analysis methods (e.g., like Temporal Fourier Transforms of camera pixel values in the areas where the highest reddening signal is likely to occur). It is noted that the aforementioned vitals may contribute directly to the Stress scale value. For example, if these vital values are found to be in the higher regions (e.g., higher than the normal value) over a period of time (e.g., a minute), then the Stress scale value may indicate a high chance of being stressed.

Figure 9:
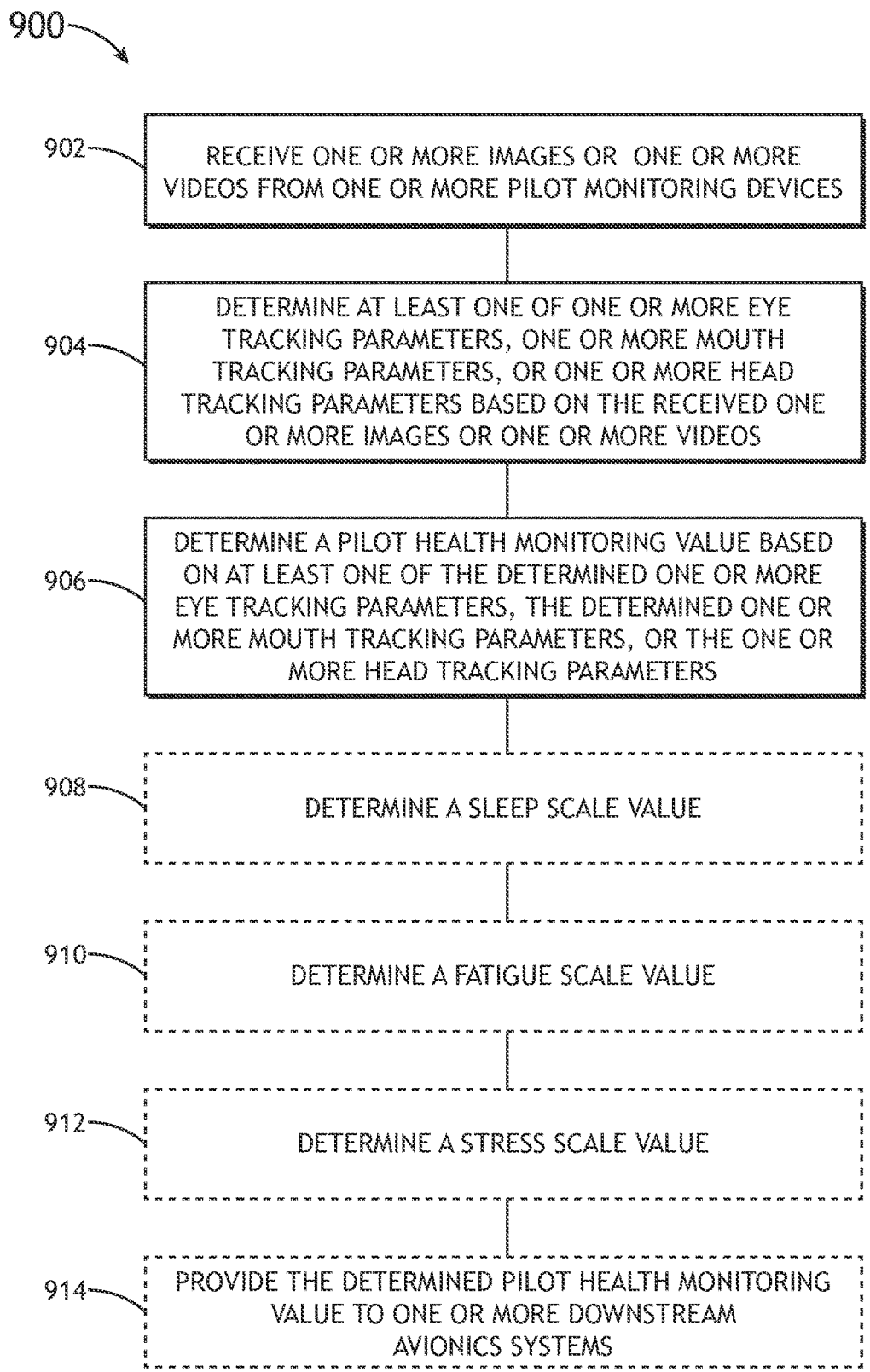
FIG. 9 illustrates a flowchart depicting a method or process for non-invasive operator health monitoring, in accordance with one or more embodiments of the disclosure.

FIG. 9 illustrates a flow diagram depicting a method or process 900 of determining one or more pilot monitoring values, in accordance with one or more embodiments of the present disclosure.

In a step 902, at least one of one or more images or one or more videos may be received. For example, the one or more controllers 106 may be configured to receive the one or more images or the one or more videos, including the tracked facial features, from the one or more pilot monitoring devices.

In a step 904, one or more biometric parameters may be determined based on the received one or more images or videos. For example, the one or more controllers 106 may be configured to determine at least one of one or more eye tracking parameters, one or more mouth tracking parameters, or one or more head tracking parameters based on the receive one or more mages or one or more videos.

In a step 906, one or more pilot health monitoring values may be determined. For example, the one or more controllers 106 may be configured to determine one or more pilot health monitoring values based on at least one of the determined one or more eye tracking parameters, the determined one or more mouth tracking parameters, or the one or more head tracking parameters. In one instance, the one or more controllers 106 may be configured to determine one or more pilot health monitoring values based on at least one of the determined one or more eye tracking parameters, the determined one or more mouth tracking parameters, or the one or more head tracking parameters using a rule-based/machine learning algorithm stored in the memory of the one or more controllers. In another instance, the one or more controllers 106 may be configured to determine one or more pilot health monitoring values based on at least one of the determined one or more eye tracking parameters, the determined one or more mouth tracking parameters, or the one or more head tracking parameters using one or more predetermined thresholds of a database stored in the memory of the one or more controllers.

The one or more pilot health monitoring values includes at least one of a sleep scale value, a fatigue scale value, or a stress scale value.

In a step 908, a sleep scale value may be determined. For example, the one or more controllers 106 may be configured to determine a sleep scale value based on the determined one or more biometric parameters.

In a step 910, a fatigue scale value may be determined. For example, the one or more controllers 106 may be configured to determine a fatigue scale value based on the determined one or more biometric parameters and one or more detected emotions.

In a step 912, a stress scale value may be determined. For example, the one or more controllers 106 may be configured to determine a stress scale value by determining a skin intensity value of at least one of the pilot's forehead or the pilot's cheeks and then determining at least one a pulse rate, a blood pressure, or a respiration rate based on the determined skin intensity value along with an emotion detected. The one or more controllers 106 may be configured to determine at least one a pulse rate, a blood pressure, a respiration rate based on the determined skin intensity value by deriving a power spectrum, as described previously herein. It is noted that unlike existing monitoring systems which use invasive measurement devices, the system 100 may be configured to non-invasively detect east one a pulse rate, a blood pressure, or a respiration rate using vision-based pilot monitoring devices 102.

In an optional step 914, the determined one or more pilot monitoring values may be provided to one or more downstream avionics systems. For example, the one or more controllers 106 may be configured to provide the one or more determined pilot monitoring values to one or more downstream avionics controllers. In this regard, if the system determines that the pilot has poor alertness or poor health, the one or more controllers 106 may provide such status to one or more downstream avionics controllers (e.g., external air traffic control or airline monitoring centers). As such, the one or more downstream avionics controllers may adjust one or more function of the aircraft if it is determined that the pilot is incapacitated.

Although one or more embodiments of the present disclosure are directed to an a pilot health monitoring system for an aircraft, it is noted herein that the system and method may be directed for monitoring a health status for any type of vehicle operator environment.

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

Although inventive concepts have been described with reference to the embodiments illustrated in the attached drawing figures, equivalents may be employed and substitutions made herein without departing from the scope of the claims. Components illustrated and described herein are merely examples of a system/device and components that may be used to implement embodiments of the inventive concepts and may be replaced with other devices and components without departing from the scope of the claims. Furthermore, any dimensions, degrees, and/or numerical ranges provided herein are to be understood as non-limiting examples unless otherwise specified in the claims.

What is claimed:

1. A system, the system comprising:
   one or more pilot monitoring devices configured to track one or more facial features of a pilot, the one or more tracked facial features including at least one of a pilot's eyes, a pilot's mouth, a pilot's head posture, a pilot's forehead, or a pilot's cheek, the one or more pilot monitoring devices configured to generate at least one of one or more images or one or videos of the tracked one or more facial features of the pilot; and
   one or more controllers communicatively coupled to the one or more imaging devices, the one or more controllers including one or more processors configured to execute a set of program instructions stored in memory, the set of program instructions configured to cause the one or more processors to:
      receive the at least one of the one or more images or the one or more videos from the one or more pilot monitoring devices;
      determine at least one of one or more eye tracking parameters, one or more mouth tracking parameters, one or more head tracking parameters, or an emotion of the pilot based on the received one or more images or one or more videos;
      determine a color skin intensity value of at least one of the pilot's forehead or the pilot's cheek;
      determine at least one of a pulse rate, a blood pressure, or a respiratory rate based on the determined skin intensity value by deriving a power spectrum of one or more pixel values computed from at least one of the pilot's forehead or the pilot's cheek; and
      determine a pilot health monitoring value based on at least one of the determined one or more eye tracking parameters, the determined one or more mouth tracking parameters, the one or more head tracking parameters, or the determined emotion of the pilot, wherein the pilot health monitoring value includes a stress score.

2. The system of claim 1, wherein the one or more pilot monitoring devices includes one or more cameras.

3. The system of claim 2, wherein the one or more cameras includes one or more cockpit cameras.

4. The system of claim 2, wherein the one or more cameras includes one or more head worn device cameras.

5. The system of claim 1, wherein the one or more processors are configured to determine the pilot health monitoring value based on at least one of the determined one or more eye tracking parameters, the determined one or more mouth tracking parameters, the one or more head tracking parameters, or the determined emotion of the pilot using one of a rule-based algorithm or a machine learning model stored in the memory of the one or more controllers.

6. The system of claim 1, wherein the one or more processors are configured to determine the pilot health monitoring value based on at least one of the determined one or more eye tracking parameters, the determined one or more mouth tracking parameters, or the one or more head tracking parameters using one or more predetermined thresholds stored in the memory of the one or more controllers.

7. The system of claim 1, wherein the one or more eye tracking parameters include at least one of:
a blink frequency, a percentage of eye lid closure, an average eye closure, a blink type, an average eye closure speed, an interblink duration, an eye gaze state, or an eye gaze frequency.

8. The system of claim 1, wherein the one or more mouth tracking parameters include a yawn frequency.

9. The system of claim 1, wherein the one or more head tracking parameters include a head tilt angle.

10. The system of claim 1, wherein the pilot health monitoring value includes a sleep scale score.

11. The system of claim 1, wherein the pilot health monitoring value includes a fatigue scale score.

12. A method, the method comprising:
receiving at least one of one or more images or one or more videos of one or more tracked facial features of a pilot from one or more pilot monitoring devices, the one or more tracked facial features including at least one of a pilot's eyes, a pilot's mouth, a pilot's head posture, a pilot's forehead, or a pilot's cheek;

determining at least one of one or more eye tracking parameters, one or more mouth tracking parameters, one or more head tracking parameters, or an emotion of the pilot based on the received one or more images or one or more videos;

determining a color skin intensity value of at least one of the pilot's forehead or the pilot's cheek;

determining at least one of a pulse rate, a blood pressure, or a respiratory rate based on the determined skin intensity value by deriving a power spectrum of one or more pixel values computed from at least one of the pilot's forehead or the pilot's cheek; and determining a pilot health monitoring value based on at least one of the determined one or more eye tracking parameters, the determined one or more mouth tracking parameters, the one or more head tracking parameters, or the determined emotion of the pilot, wherein the pilot health monitoring value includes a stress score.

\* \* \* \* \*